United States Patent [19]

Brighty

[11] Patent Number: 4,782,146

[45] Date of Patent: Nov. 1, 1988

[54] PROCESS FOR THE SYNTHESIS OF PENEMS

[75] Inventor: Katherine E. Brighty, Groton, Conn.

[73] Assignee: Pfizer Inc., New York, N.Y.

[21] Appl. No.: 62,798

[22] Filed: Jun. 16, 1987

Related U.S. Application Data

[62] Division of Ser. No. 891,493, Jul. 29, 1986, Pat. No. 4,695,626.

[51] Int. Cl.$^4$ .................. C07D 499/00; A61K 31/425
[52] U.S. Cl. .................................................... 540/310
[58] Field of Search ................. 540/310; 514/192, 195

[56] References Cited

U.S. PATENT DOCUMENTS 3,835,130 9/1974 Woodward .......................... 260/243
4,585,874 4/1986 Alpegiani et al. ................... 260/243

OTHER PUBLICATIONS

Leanza et al., Tetrahedron 39, pp. 2505–2513 (1983).
Ganguly et al., Journal of Antimicrobial Chemotherapy 9, Suppl. C, pp. 1–6 (1982).

Primary Examiner—Nicholas S. Rizzo
Attorney, Agent, or Firm—Peter C. Richardson; J. Trevor Lumb; Robert K. Blackwood

[57] ABSTRACT

A process for the synthesis of penems from azetidinones via 1-aza-4,5-dithiabicyclo[4.2.0]oct-2-en-8-one-2-carboxylate esters.

11 Claims, No Drawings

PROCESS FOR THE SYNTHESIS OF PENEMS

This is a division, of application Ser. No. 891,493, filed on July 29, 1986, now U.S. Pat. No. 4,695,626.

BACKGROUND OF THE INVENTION

The present invention is directed to processes for the conversion of 3R,4R-4-acetoxy-3-[1R-1-(t-butyldimethylsilyloxy)ethyl]-2-azetidinone to a penem allyl ester of the formula

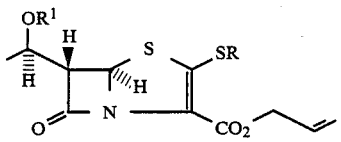

where R is $(C_1-C_5)$alkyl or 1-oxo-3-thiolanyl of the formula

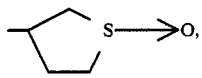

and $R^1$ is a conventional hydroxy-protecting group. In particular the invention is directed to the final stages in which an appropriately substituted 2-chloro-2-((2-azetidinon-1-yl)acetate is converted to the compound (I), in part via the intermediate of the formula

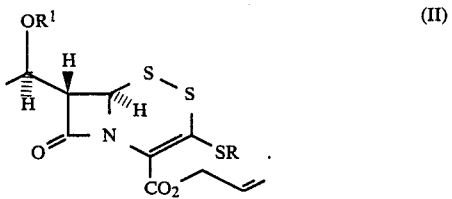

The most preferred compound prepared by means of the present process is the compound of the formula (I) which is an approximately 1:1 mixture of diastereoisomers in which R is (cis-1-oxo-3-thiolanyl), i.e., the thiolane ring substituents are cis relative to each other, and $R^1$ is t-butyldimethylsilyl. The silyl protecting group and allyl ester are readily cleaved to yield the corresponding 5R,6S-6-(1R-1-hydroxyethyl)2-(cis-1-oxo-3-thiolanylthio)-2-penem-3-carboxylate, a compound first described in European Patent Application No. 130025, which further discloses the method of using this compound as an antibacterial agent. The method of synthesis disclosed in EP 130025 is highly versatile, permitting the facile synthesis of a wide variety of analogs. However, for individual compounds, particularly the above preferred cis compound, a more direct synthesis comprising fewer chemical steps is highly desirable.

When R is $(C_1-C_5)$alkyl, the intermediates of the formula (I) are likewise converted by conventional hydrolytic methods to other valuable penem antibiotics and/or beta-lactamase inhibitors such as Sch 29482:

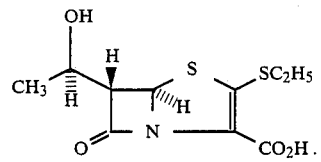

See Ganguly et al., J. Antimicrob. Chemotherapy. 9, Supplement C, pp. 1-6 (1982).

The present intermediate compounds of the formula (I) wherein $R^1$ is t-butyldimethylsilyl and R is ethyl, propyl, butyl, isobutyl or t-butyl are known compounds [Leanza et al., Tetrahedron 39, pp. 2505-2513 (1983)].

The present intermediates of the formula (I) are converted to known penem antibiotics (e.g., Ganguly et al., loc. cit.; Hamanaka, European Patent Application No. 130,025; Daniels et al., J. Chem. Soc., Chem. Commun. 1982 pp. 1119-1120; Tanaka et al., ibid., pp. 713-714) according to known methods for the removal of allyl ester protecting groups [e.g., Ganguly et al., loc. cit.; Girijavallabhan et al., Tetrahedron Lett. 22, pp. 3485-3488 (1981); Jeffrey et al., J. Org. Chem. 47, pp. 587-590 (1982)] and for removal of silyl protecting groups [e.g., Hayashi et al., Chem. Pharm. Bull. 29, pp. 3158-3172 (1981)].

SUMMARY OF THE INVENTION

Attractive precursors for the above compounds of the formula (I) are the 4-acetoxy-2-azetidinones of the formula

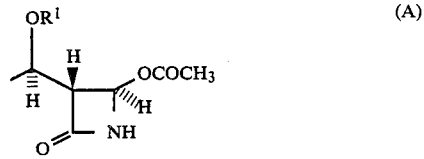

where $R^1$ is as defined above. For example, the compound wherein $R^1$ is t-butyldimethylsilyl is readily available from 6-amino-penicillanic acid by the method of Leanza et al., loc. cit.

According to the present invention, the compounds of the formula (A) are first reacted with sodium [$(C_1-C_5)$alkyl or 1-oxo-3-thiolanyl]trithiocarbonate and then with allyl glyoxylate to form a compound of the formula

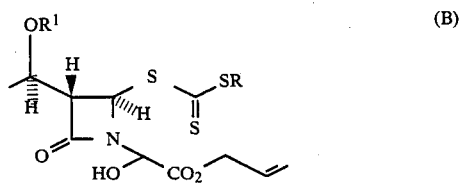

and then with $SOCl_2$ or $CH_3SO_2Cl$ and a tertiary amine to form a compound of the formula

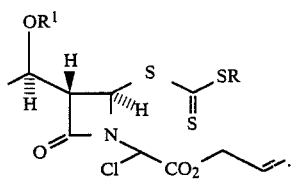

The present invention is specifically directed to the unconventional process steps of converting a compound of the formula (III) to a compound of the formula (I), as defined above, which comprises:

(a) treating the compound of the formula (III) with base in a reaction-inert solvent at −80° to 40° C. to produce a mixture comprising the compound of the formula (I) and a compound of the formula (II), as defined above, and (b) desulfurization of the compound of the formula (II) with

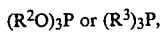

wherein each $R^2$ is the same or different and selected from $(C_1-C_4)$alkyl and each $R^3$ is the same or different and selected from $(C_1-C_4)$alkyl or phenyl, at −50° to 40° C. in the same or a second reaction-inert solvent, to form additional compound of the formula (I).

The intermediate compound of the formula (II) can be isolated, and optionally separated from the compound (I) formed in step (a). However, it is preferred to carry out steps (a) and (b) as a "one-pot" process in a common solvent without isolation of the compound (II). The compound (III) can also be conveniently carried into the process without purification.

As used herein, the expression "reaction-inert solvent" refers to a solvent which does not interact with reactants, intermediates or products in a manner which adversely affects the yield of the desired products. It should be noted that preferred solvents, as noted below, which favorably affect the yield by reducing the level of undesired byproducts are considered reaction-inert according to this definition.

The present invention is also directed to intermediate compounds of the formula (II), per se.

The preferred hydroxy-protecting group ($R^1$) is t-butyldimethylsilyl, although other conventional hydroxy-protecting groups, particularly other silyl ether forming groups can of course be substituted therefor. The preferred values of R are cis-1-oxo-3-thiolanyl and t-butyl, most particularly the former.

The preferred base for step (a) is 1,8-diazabicyclo[5.4.0]undec-7-ene (DBU), preferably in acetonitrile as solvent, generally at a temperature somewhat higher in the specified range, e.g., at or near 0° C.

The preferred reagent for step (b) is triphenylphosphine, in acetonitrile when the intermediate (II) where R is 1-oxo-3-thiolanyl is isolated, in hexane when the intermediate (II) where R is t-butyl is isolated, and in the preferred acetonitrile of step (a) when the intermediate (II) is not isolated.

All structural formulas herein are intended to depict the absolute stereochemical configuration of the present optically active compounds.

DETAILED DESCRIPTION OF THE INVENTION

The present invention is readily carried out. The intermediate compounds of the formula (III) are prepared from the azetidinones of the formula (A) by conventional methods, as exemplified in Preparations detailed below.

The intermediates (III) are first converted to a mixture comprising the further intermediate (II) and the desired compound (I), by the action of a substantially one equivalent of a strong, anhydrous base of low nucleophilicity. Such bases include sodium hydride, potassium t-butoxide and most preferred DBU, as noted above. Temperature is not highly critical, but is preferably in the range of −80° to 40° C. to minimize side reactions; most preferred are temperatures in the mid to upper portion of the range, e.g., near 0° C. Solvent is not critical, although polar solvents are preferred. The ratio of the compound (II)/(I) also varies with solvent, but that is not a critical factor since the compound (II) is converted to (I) in the final step. The most preferred solvent is acetonitrile, or acetonitrile containing a minor portion (e.g., 5% by volume) of isopropanol. The starting material (III) can be utilized in this reaction in crude form, i.e., as directly isolated from a reaction mixture without further purification.

If desired, the product mixture comprising (I) and (II) can be isolated, and if further desired, separated into its pure components, e.g., by column chromatography on silica gel. However such isolation and separation is unnecessary. To minimize effort, the reaction solution can be simply introduced into the final stage of the process, wherein the compound (II) is converted to additional compound (I). Where the intermediates are not isolated, the preferred solvent is acetonitrile.

In the second and final stage of the process, the intermediate (II) is converted to additional desired compound (I), accompanied by undesired 5-epimer. This conversion is accomplished by the action of at least one molar equivalent of phosphine or phosphite, as defined above. The preferred reagents are triphenylphosphine and trimethyl phosphite, since they generally produce less 5-epimer. Temperature is not highly critical, but is preferably in the range of −40° to 40° C., conveniently at the midpoint of this range, i.e., near 0° C. The proportion of the desired compound (I) to its 5-epimer generally varies with the solvent. Preferred solvents are noted above.

The utility of other solvents in the present transformation is determined by simple experiment. As noted above, present compounds (I) are converted to known and valuable penems by conventional methods.

The present invention is illustrated by the following examples. However, it should be understood that the invention is not limited to the specific details of these examples.

EXAMPLE 1

Allyl 6R,7S-3-(cis-1-Oxo-3-thiolanylthio)-7-[1R-(t-butyldimethylsilyloxy)ethyl]-1-aza-4,5-dithiabicyclo[4.2.0]oct-2-en-8-one-2-carboxylate and Allyl 5R,6S-6-[1R-1-(t-Butyldimethylsilyloxy)ethyl]-2-(cis-1-oxo-3-thiolanylthio)-2-penem-3-carboxylate

[Compounds (II) and (I), respectively, where R is cis

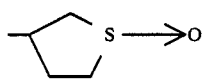

and $R^1$ is tBuSiMe$_2$]

Method A

The product of Preparation 4 (39.6 mg, 0.069 mmol) was dissolved in 2 ml tetrahydrofuran, NaH (60% suspension in mineral oil, 28 mg, 0.69 mmol) was added, and the mixture stirred at ambient temperature for 0.5 hour under dry $N_2$. The mixture was poured into 10 ml saturated $NH_4Cl$, stirred for 20 minutes, diluted with 8 ml ethyl acetate and the organic layer separated, washed with brine, dried over $Na_2SO_4$ and stripped to an oil, 32 mg. The latter was chromatographed on silica gel, using 1:1 ethyl acetate:hexane as eluant. Least polar fractions contained mineral oil and undesired by-product, 10.4 mg; tlc Rf 0.65 and 0.75 (ethyl acetate). Intermediate fractions gave title dithiabicyclooctenone product, 1.6 mg; tlc Rf 0.45 (ethyl acetate);and more polar fractions gave title penem product, 2.4 mg; tlc Rf 0.25 (ethyl acetate).

Method B

The product of Preparation 4 (136 mg, 0.237 mmol) was dissolved in 7 ml dry $CH_3CN$ (freshly distilled from $CaH_2$) and cooled to 0° C. DBU (1,8-Diazabicyclo[5.4.0]undec-7-ene; 36 mg, 0.035 ml, 0.237 mmol; freshly distilled from $CaH_2$) was added dropwise. After stirring 45 minutes at 0° C., the mixture was quenched with 15 ml saturated $NH_4Cl$ and diluted with 20 ml of ethyl acetate. The organic layer was separated, washed with 15 ml saturated $NH_4Cl$, 15 ml $H_2O$ and 15 ml saturated brine, dried over $Na_2SO_4$ and stripped to an oil, 128 mg, which was chromatographed on silica gel using ethyl acetate as eluant. Less polar fractions gave title dithiabicyclooctenone product, 84.2 mg; tlc Rf 0.45 (ethyl acetate);

$^1$H-NMR(CDCl$_3$)delta(ppm): 0.07 and 0.08 (2s, 6H), 0.87 (s, 9H), 1.26 (d, J=6.3, 3H), 2.60–3.14 (m, 5H), 3.25 (dd, apparent t, J=3.2, 1H), 3.55–3.80 (m, 2H), 4.33–4.42 (m, 1H), 4.70–4.89 (m, 3H), 5.27–5.44 (m, 2H), 5.91–6.08 (m, 1H).

More polar fractions gave title penem product, 15.8 mg; tlc Rf 0.25 (ethyl acetate); $^1$H-NMR(CDCl$_3$)300 MHz delta(ppm): 0.08 (s, 6H), 0.88 (s, 9H), 1.25 (d, 3H, J=6.3 Hz), 2.6–2.9 (m, 4H), 3.13 (m, 1H), 3.64 (m, 1H), 3.70 and 3.72 (2dd, 1H, J=1.5, 4.7 Hz), 3.84 and 3.97 (2dd, 1H, J=8.4, 14.2 Hz), 4.24 (m, 1H), 4.70 (m, 2H), 5.24 (dd, 1H, J=1.3, 10.5 Hz), 5.40 (dd, 1H, J=1.3, 17.1 Hz), 5.63 and 5.65 (2d, 1H, J=1.5 Hz), 5.93 (ddt, 1H, J=5.6, 10.5, 17.1 Hz).

Method B was repeated in other solvents with the following results:

| Solvent | Yield | Ratio (II)/(I) |
| --- | --- | --- |
| acetonitrile | 79% | 5:1 |
| tetrahydrofuran | 61% | 2.6:1 |
| dimethylsulfoxide | 73% | 4:1 |
| isopropanol | 54% | 1.2:1 |
| 5% isopropanol in acetonitrile | 83% | 2:1 |

Method C

Title product of Preparation 3 (0.533 g, 0.963 mmol) was converted to title product of Preparation 4 by the method of that Preparation. After bicarbonate extraction, drying and stripping, the residual oil, 0.508 g, was taken up in 26 ml dry $CH_3CN$, chilled to 0° C. under $N_2$ and DBU (0.133 ml, 0.135 g, 0.888 mmol) added. After 40 minutes, present mixed title products were recovered according the Method B immediately above, producing crude title products as an oil, 0.48 g and, after chromatography, purified title dithiabicyclooctenone, 0.218 g, and purified title penem product, 49.3 mg.

EXAMPLE 2

Allyl 5R,6S-6-[1R-1-(t-Butyldimethylsilyloxy)ethyl]-2-(cis-1-oxo-3-thiolanylthio)-2-penem-3-carboxylate

Method A

Title dithiabicyclooctenone product of the preceding Example (54.5 mg, 0.101 mmol) was dissolved in 5.5 ml of $CH_3CN$ and cooled to 0° C. under $N_2$. $(C_6H_5)_3P$ (27 mg, 0.101 mmol) was added in one portion. After 5 minutes the reaction mixture was stripped to dryness and the residue chromatographed on silica gel using ethyl acetate as eluant to yield less polar 5-epimer of title product as an oil, 8.5 mg, and the desired more polar title product as a white solid, 39.3 mg, identical with the same product of the preceding Example.

Method A was repeated, varying the solvent and reducing agent with the following results:

| Reducing Agent | Solvent | Total Yield of Title Product and 5-Epimer | Ratio of Title Product: 5-Epimer |
| --- | --- | --- | --- |
| P(C$_6$H$_3$)$_3$ | ether | 31% | — |
| P(C$_6$H$_5$)$_3$ | CH$_2$Cl$_2$ | 53% | 8–10:1 |
| P(C$_6$H$_5$)$_3$ | THF$^a$ | 76% | 12:1 |
| P(C$_6$H$_5$)$_3$ | (iPr)$_2$O | 80%$^b$ | 8:1 |
| P(C$_6$H$_5$)$_3$ | anisole | 81% | 9:1 |
| P(C$_6$H$_5$)$_3$ | toluene | 86% | 8:1 |
| P(C$_6$H$_5$)$_3$ | CH$_3$CN | 90% | 6:1 |
| PCH$_3$(C$_6$H$_5$)$_2$ | CH$_3$CN | 81% | 5–6:1 |
| PC$_6$H$_5$(CH$_3$)$_2$ | CH$_3$CN | 82% | 1:1 |
| P(C$_2$H$_5$)$_3$ | CH$_3$CN | 95% | 1:1 |
| P(n-C$_4$H$_9$)$_3$ | CH$_3$CN | 75% | 1:2 |
| P(OCH$_3$)$_3$ | THF$^a$ | 57% | 14:1 |

$^a$tetrahydrofuran
$^b$more than 90% of the product, contaminated with a little P(C$_6$H$_5$)$_3$ crystallized directly from the reaction mixture.

Method B

Title product of Preparation 4 (0.368 g, 0.643 mmol) was converted to mixed title products of Example 1 by Method B of that Example. After stripping the dried organic layer, the residual oil, 0.338 g was taken up in 70 ml CH$_3$CN and cooled to 0° C. P(C$_6$H$_5$)$_3$ (0.175 g, 0.643 mmol) was added in one portion, the mixture stirred 10 minutes, and stripped to a second oil (0.481 g) which was chromatographed as in Method A, immediately preceding, to yield 11.2 mg of the 5-epimer of title product and 0.189 g of desired title product, identical with the same product of Example 1.

Method C

Title product of Preparation 3 (0.602 g, 1.09 mmol) was converted to the title product of Preparation 4 by the method of that Preparation. After bicarbonate extraction, drying and stripping, the residual oil, 0.586 g was taken up in 30 ml dry $CH_3CN$, cooled to 0° C. under $N_2$ and reacted with DBU, 0.153 ml, according to Method B of Example 1. After 40 minutes at 0° C., $P(C_6H_5)_3$ (0.279 g, 1.02 mmol) was added in one portion. After 5 minutes, the reaction mixture was worked up with aqueous $NH_4Cl$ quench and ethyl acetate extraction according to the Method B of Example 1 to yield crude title product as an oil. The latter was chromatographed according to Method A of the present Example to yield crude 5-epimer, 67 mg, and purified title product, 0.249 g, identical with the same product of Example 1.

EXAMPLE 3

Allyl 6R,7S-3-(t-Butylthio)-7-[1R-(t-butyldimethylsilyloxy)ethyl]-1-aza-4,5-dithiabicyclo[4.2.0]oct-2-en-8-one-2-carboxylate and Allyl 5R,6S-6-[1R-(t-Butyldimethylsilyloxy)ethyl]-2-(t-butylthio)-2-penem-3-carboxylate [Compounds (II) and (I), respectively, where R is t-butyl and $R^1$ is $Me_2SitBu$]

Title product of Preparation 7 (26 mg, 0.049 mmol) was taken up in 0.3 ml dry THF and added via syringe to a stirred slurry of NaH (20 mg of 60% by weight in mineral oil, 0.5 mmol) in 1.2 ml dry THF at 30° C. The temperature was increased to 40° C. and stirred for 15 minutes, then quenched with 5 ml saturated $NH_4Cl$ and extracted with 10 ml ethyl acetate. The organic extract was dried over $Na_2SO_4$, stripped and the residue chromatographed using 5:1 hexane:ethyl acetate as eluant to yield less polar dithiabicyclooctenone title product, 8 mg; tlc Rf 0.5 (5:1 hexane:ethyl acetate); $^1$H-NMR($CDCl_3$)delta(ppm): 0.07 (s, 3H), 0.08 (s, 3H), 0.87 (s, 9H), 1.26 (d, J=6.3, 3H), 1.40 (s, 9H), 3.23 (dd, J=3.7, 2.8, 1H), 4.33–4.43 (m, 1H), 4.78 (d, J=2.7, 1H), 4.68–4.86 (m, 2H), 5.25–5.42 (m, 2H), 5.91–6.07 (m, 1H); and more polar title penem product, 11 mg; tlc Rf 0.4 (5:1 hexane:ethyl acetate); $^1$H-NMR($CDCl_3$)delta(ppm): 0.07 (s, 3H), 0.08 (s, 3H), 0.88 (s, 9H), 1.25 (d, J=6.3, 3H), 1.52 (s, 9H), 3.69 (dd, J=4.5, 1.5, 1H), 4.20–4.27 (m, 1H), 4.60–4.78 (m, 2H), 5.19–5.45 (m, 2H), 5.55 (d, J=1.4, 1H), 5.86–5.99 (m, 1H).

EXAMPLE 4

Allyl 5R,6S-6-[1R-(t-Butyldimethylsilyloxy)ethyl]-2-(t-butylthio)-2-penem-3-carboxylate Method A Title product of Preparation 7 (0.205 g, 0.390 mmol) was taken up in 5.5 ml dry THF and cooled under $N_2$ to −78° C. Potassium t-butoxide (0.390 ml of 1.0M solution in THF) was added dropwise. After 35 minutes at −78° C., the reaction was quenched with 6 ml saturated $NH_4Cl$ and diluted with 25 ml of hexane. The organic layer was separated and evaporated under a stream of nitrogen to 10 ml. Tlc (5:1 hexane:ethyl acetate) indicated a 1:1 mixture of title product (Rf 0.4) and the dithiabicyclooctenone of Example 1 (Rf 0.5). To the latter mixture in 10 ml hexane, under $N_2$ at room temperature was added trimethyl phosphite (0.060 ml). After 18 hours, a second like portion of trimethyl phosphite was added, and after another 0.5 hour, the solution chromatographed on silica gel with 9:1 hexane:ethyl acetate as eluant to yield purified title product identical with the same product in Example 3.

Method B

Title dithiabicyclooctenone product of Example 3 (8 mg, 0.016 mmol) was taken up in 0.164 ml hexane under $N_2$. Triisopropyl phosphite (0.008 ml, 0.032 mmol) was added via syringe. After 10 minutes, the reaction mixture was stripped. The residue comprised title product and its 5-epimer in about a 2:1 ratio by 300 MHz $^1$H-NMR, separable by chromatography according to method A immediately above.

Method C

Title dithiabicyclooctenone product of Example 3 (13 mg, 0.027 mmol) was taken up in 0.5 ml hexane, $P(C_6H_5)_3$ (10 mg, 0.04 mmol) was added and the mixture warmed to 40° C. After 0.5 hour, more $P(C_6H_5)_3$ (12.5 mg, 0.05 mmol) was added and the temperature maintained at 40° C. for an additional 15 minutes, and the reaction mixture then stripped. The residue comprised title product and its 5-epimer in 5:1 ratio by $^1$H-NMR.

Substitution of $CH_3CN$ for hexane gave title product and its 5-epimer in 2:3 ratio by $^1$H-NMR, while substitution of $CH_3OH$ for hexane gave title product and its 5-epimer in 2:7 ratio by $^1$H-NMR.

EXAMPLE 5

Allyl 5R,6S-6-(1R-1-Hydroxyethyl)-2-(cis-1-oxo-3-thiolanylthio)-2-penem-3-carboxylate A flame-dried, three-neck flask equipped with a thermometer and two addition funnels under a $N_2$ atmosphere was charged with the product of Example 2 (20 g, 0.0397 mol) and 65 ml dry tetrahydrofuran. The reaction was cooled to an internal temperature of 5° C. and 23.8 g (0.397 mmol) of glacial acetic acid was added dropwise over a fifteen minute period keeping the internal temperature at 5° C. Tetrabutyl ammonium fluoride in tetrahydrofuran (1M, 119 ml) was added dropwise over a one hour period keeping the internal temperature at 5° C. The reaction was allowed to slowly warm to room temperature and stirred an additional sixteen hours at room temperature. The reaction was poured into 2000 ml iced $H_2O$ and extracted 3×1000 ml ethyl acetate. The combined organic extracts were washed 3×650 ml $H_2O$, 2×650 ml saturated $NaHCO_3$ and 2×650 ml brine, dried over $Na_2SO_4$, filtered and concentrated in vacuo to dryness. The residue was chromatographed on silica gel with 1:19 $CH_3OH$:ethyl acetate as eluant, 13.3 g.

$^1$H-NMR($CDCl_3$)300 MHz: 1.36 (d, 3H, J=6.2 Hz), 2.46 and 2.51 (2 br d, 1H), 2.6–2.9 (m, 4H), 3.14 (m, 1H), 3.6–3.8 (m, 2H), 3.81 and 3.93 (2dd, 1H, J=8, 14 Hz), 4.23 (m, 1H), 4.66 (dd, 1H, J=5.6, 13 Hz), 4.77 (dd, 1H, J=5.6, 13 Hz), 5.25 (d, 1H, J=10.5 Hz), 5.41 (d, 1H, J=17.1 Hz), 5.67 and 5.70 (2s, 1H), 5.94 (ddt, 1H, J=5.6, 10.5, 17.1).

IR(KBr) cm$^{-1}$: 3233, 1767, 1681, 1495, 1316, 1201, 1124.

By the same method the product of Example 4 is converted to allyl 5R,6S-6-(1R-1-hydroxyethyl)-2-(t-butylthio)-2-penem-3-carboxylate.

EXAMPLE 6

Sodium 5R,6S-6-(1R-1-Hydroxyethyl)-2-(cis-1-oxo-3-thiolanylthio)-2-penem-3-carboxylate A flame dried flask wrapped in aluminum foil under an argon atmosphere is charged with the product of the preceding Example (16.7 g, 43 mmol) in 400 ml of degassed $CH_2Cl_2$, triphenylphosphine (1.69 g, 6.5 mmol), sodium 2-ethylhexanoate (60.1 ml of 0.82M in ethyl acetate, 49 mmol) and tetrakis(triphenylphosphine)palladium (3.69 g, 3.2 mmol). The reaction is stirred at room temperature for seventy minutes, an additional 350 mg tetrakis(triphenylphosphine)palladium is added and the reaction stirred at room temperature an additional twenty-five minutes. Degassed ethyl acetate (275 ml) is added to the reaction over a six minute period. The reaction is stirred at room temperature for thirty minutes, filtered and the solids briefly air-dried, then slurried with 180 ml acetone for thirty minutes, filtered and dried to afford about 15.3 g (97%) of product as a yellow solid as a mixture of two diastereoisomers, corresponding to the cis-1-oxo-3-thiolanyl isomer of Example 2, page 20 of European Patent Application 130,025.

By the same method, the t-butylthio product of the preceding Example is converted to sodium 5R,6S-6-(1R-1-hydroxyethyl)-2-(t-butylthio)-2-penem-3-carboxylate in similar yield.

PREPARATION 1

Allyl Glyoxylate Monohydrate

Diallyl tartrate (23.9 g, 0.104 mol) was dissolved in 500 ml ether and cooled to 0° C., stirring under $N_2$. Periodic acid (47.3 g, 0.298 mol) was added in one portion. After 2.5 hours at 0° C., solids were separated by decantation and filtration. The filtrate was washed 3×250 ml saturated $Na_2S_2O_3$ and the further solids which formed removed by a second filtration. The second filtrate was dried over $Na_2SO_4$ and stripped to an oil, 17.8 g, which was triturated twice with ether, twice filtered and separated from the ether to form a second oil, 15.6 g. The latter was flash chromatographed on silica gel, monitoring by tlc and using 2:1 hexane:ethyl acetate as eluant, discarding early fractions containing a slightly less polar impurity. Purified title product was recovered as an oil, 11.3 g, tlc Rf 0.25 (2:1 hexane:ethyl acetate).

PREPARATION 2

3S,4R-3-[1R-1-(Dimethyl-t-butylsilyloxy)ethyl]-4-[cis-1-oxo-3-throlanylthio(thiocarbonyl)thio]-2-azetidinone A flame-dried, three-neck flask equipped with a mechanical stirrer, dropping funnel and low temperature thermometer under a $N_2$ atmosphere was charged with racemic, cis-3-(acetylthio)thiolane 1-oxide (4.26 g, 23.9 mmol) and 90 ml isopropyl alcohol. The reaction was cooled to an internal temperature of −20° C. and sodium methoxide (1.18 g, 21.9 mmol) was added in one portion. The reaction was stirred at −20° to −25° C. for ninety minutes, then allowed to warm to −10° C. The reaction was recooled to −30° C. and a solution of carbon disulfide (7.94 g, 104 mmol) in 30 ml isopropyl alcohol was added dropwise over a thirty minute period. The reaction was stirred at −25° to −30° C. for forty minutes. A solution of 3R,4R-4-acetoxy-3-[1R-1-(dimethyl-t-butylsilyloxy)ethyl]-2-azetidinone [6 g, 20.9 mmol; Leanza et al., Tetrahedron 39, pages 2505–2513 (1983)] in 54 ml isopropyl alcohol was added dropwise over a thirty-minute period. The reaction was stirred at −20° C. for thirty minutes, then allowed to warm to 0° C. and stirred at 0° to 1° C. for ninety minutes. The reaction was quenched with 150 ml saturated ammonium chloride solution, and then 200 ml ethyl acetate was added. The mixture was transferred to a separatory funnel and 150 ml brine was added. The organic layer was separated and the aqueous layer was extracted with an additional 200 ml ethyl acetate. The combined ethyl acetate extracts were washed two times with 100 ml portions brine. The organic layer was cooled to 5° C. and dried over $MgSO_4$, then filtered and concentrated in vacuo to yield a viscous oil. The oil was azeotroped four times with 50 ml portions of methylene chloride and pumped under high vacuum to yield 8.32 g (90.5%) of a yellow foam comprising a mixture of two title diastereoisomers.

An analytical sample was prepared by stirring a sample of the above foam with isopropyl ether for two hours. The yellow solids were filtered and dried, m.p. 85°–89° C. (decomposition).

Analysis calculated for $C_{16}H_{29}O_3NS_4Si$: C, 43.69; H, 6.65; N, 3.19%. Found: C, 43.41; H, 6.38; N, 3.06%.

IR(KBr) cm$^{-1}$ 1770.

$^1$H-NMR(CDCl$_3$)delta(ppm): 0.072 (s, 3H, CH$_3$Si), 0.077 (s, 3H, CH$_3$Si), 0.877 (s, 9H, t-butyl), 1.21 (d, J=6.1 Hz, 3H, CH$_3$), 2.74–3.24 (m, 6H, 3 CH$_2$), 3.78 (m, 1H, CHS), 4.29 (dd, J=6.1, 3.7 Hz, 1H, CH), 4.55 (m, 1H, CHO), 5.65 (m, 1H, CHS), 6.65 (bs, 1H, NH).

PREPARATION 3

Allyl 2R- and 2S-2-Hydroxy-2-[3S,4R-4-(cis-1-oxo-3-thiolanylthio(thiocarbonyl)thio)-3-(1R-1-(t-butyldimethylsilyloxy)ethyl)-2-azetidinon-1-yl]acetate Title product of the preceding Preparation (2.65 g, 6.03 mmol) was dissolved in 47 ml $C_6H_6$, title product of Preparation 1 (1.59 g, 12.06 mmol) added, and the mixture refluxed under $N_2$, trapping $H_2O$ with a Dean-Stark trap. After 18 hours an additional like portion of the glyoxylate was added and reflux continued for 24 hours more. The reaction mixture was concentrated to 5 ml and flash chromatographed on silica gel using ethyl acetate as eluant to produce present title product, 2.83 g; $^1$H-NMR(CDCl$_3$)delta(ppm): 0.05, 0.07 and 0.08 (3s, 6H), 0.87 and 0.88 (2s, 9H), 1.22 and 1.23 (2d, J=6.3 and 6.2, 3H), 2.72–3.01 (m, 4H), 3.14–3.22 (m, 1H), 3.33–3.40 (m, 1H), 3.66–4.05 (m, 2H), 4.23–4.32 (m, 1H), 4.55–4.77 (m, 3H), 5.28–5.41 (m, 2H), 5.13–5.18 and 5.52 (m and d, J=9.1, 1H), 5.81–6.02 (m, 1H), 6.17–6.19 and 6.26–6.28 (2m, 1H), reflecting the mixture of diastereomers.

PREPARATION 4

Allyl 2R- and 2S-2-Chloro-2-[3S,4R-4-(cis-1-oxo-3-thiolanylthio(thiocarbonyl)thio)-3-(1R-1-(t-butyldimethylsilyloxy)ethyl)-2-azetidinon-1-yl]acetate The product of the preceding Preparation (2.83 g, 5.11 mmol) was dissolved in 50 ml $CH_2Cl_2$ and cooled to 0° C. under $N_2$. Triethylamine (1.78 ml, 1.29 g, 12.8 mmol) was added followed by the dropwise addition of $CH_3SO_2Cl$ (freshly distilled from $P_2O_5$, 0.42 ml, 0.615 g, 5.4 mmol). After 1 hour at 0° C., the reaction mixture was washed 2×50 ml saturated $NaHCO_3$, 1×50 ml $H_2O$ and 1×50 ml saturated brine, dried over $Na_2SO_4$, and stripped to an oil which was flash chromatographed on silica gel with 4:1 ethyl acetate:hexane as eluant to yield present title product, 1.73 g; $^1$H-NMR($CDCl_3$)delta(ppm): 0.06 and 0.09 (2s, 6H), 0.86 and 0.89 (2s, 9H), 1.21–1.24 (m, 3H), 2.66–2.94 (m, 4H), 3.09–3.20 (m, 1H), 3.38–3.46 (m, 1H), 3.70–3.83 (m, 1H), 4.24–4.36 (m, 1H), 4.53–4.75 (m, 3H), 5.26–5.40 (m, 2H), 5.83–5.99 (m, 1H), 5.91 and 6.12 (2bs, 1H), 6.38 and 6.51 (2bs, 1H).

PREPARATION 5

3S,4R-4-[t-Butylthio(thiocarbonyl)thio]-3-[1R-1-(t-butyldimethylsilyloxy)ethyl]-2-azetidinone 3R,4R-4-Acetoxy-3-[1R-1-(t-butyldimethylsilyloxy)ethyl]-2-azetidinone (5 g, 0.0174 mol) was dissolved in 150 ml absolute ethanol and cooled to 0° C. Carbon disulfide (0.523 ml, 0.0087 mol) and then sodium t-butyl trithiocarbonate (3.28 g, 0.0174 mol) in 50 ml ethanol were added. After stirring 45 minutes, the reaction mixture was stripped, the residue taken up in 100 ml ethyl acetate, washed 1×100 ml $H_2O$ and 1×100 ml brine, dried ($Na_2SO_4$) and stripped to a pasty solid. The latter was dried in high vacuum, slurried in minimal hexane at 0° C. and filtered to yield a first crop of title product, 3.60 g. The mother liquor was stripped and slurried in minimal hexane to yield a second crop of equally pure title product, 0.49 g; tlc Rf 0.6 (1:2 ethyl acetate:hexane); $^1$H-NMR($CDCl_3$)delta(ppm): 6.57 (bs, 1H), 5.58 (d, J=2.6, 1H), 4.28 (m, 1H), 3.20 (m, 1H), 1.63 (s, 9H), 1.20 (d, J=6.3, 3H), 0.88 (s, 9H), 0.07 (s, 6H).

PREPARATION 6

Allyl 2R- and 2S-2-Hydroxy-2-[3S,4R-4-(t-butylthio(thiocarbonyl)thio)-3-(1R-1-(t-butyldimethylsilyloxy)ethyl)-2-azetidinon-1-yl]acetate Using the method of Preparation 3, with 1:5 ethyl acetate:hexane as eluant on chromatography, the product of the preceding Preparation (86.4 mg, 0.20 mmol) was converted to present title product. There was obtained 21.9 mg of less polar diastereomer; tlc Rf 0.5 (1:2 ethyl acetate:hexane); $^1$H-NMR($CDCl_3$)delta(ppm): 6.14 (d, J=3.0, 1H), 5.89 (m, 1H), 5.49 (bs, 1H), 5.30 (m, 2H), 4.63 (m, 2H), 4.26 (m, 1H), 3.34 (dd, J=4.3, 3.0, 1H), 1.62 (s, 9H), 1.19 (d, J=6.0, 3H), 0.85 (s, 9H), 0.05 (s, 3H), 0.04 (s, 3H); 17.6 mg. of mixed fractions; and 57.1 mg. of the more polar diastereomer; tlc Rf 0.45 (1:2 ethyl acetate:hexane); $^1$H-NMR($CDCl_3$)delta(ppm): 6.06 (d, J=2.7, 1H), 5.92 (m, 1H), 5.30 (m, 2H), 5.18 (s, 1H), 4.73 (m, 2H), 4.23 (m, 1H), 3.29 (m, 1H), 1.61 (s, 9H), 1.21 (d, J=6.1, 3H), 0.85 (s, 9H), 0.05 (s, 3H), 0.03 (s, 3H).

PREPARATION 7

1:1 Allyl 2R- and 2S-2-Chloro-2-[3S,4R-4-(t-butylthio(thiocarbonyl)thio)-3-(1R-1-(t-butyldimethylsilyloxy)ethyl)-2-azetidinon-1-yl]acetate Either diastereoisomeric product of the preceding Preparation gave a similar mixture of present title products. The more polar product of the preceding Preparation (57.1 mg, 0.11 mmol) and triethylamine (0.062 ml, 0.45 mmol) were dissolved in tetrahydrofuran (3 ml) at 0° C. $SOCl_2$ (0.016 ml, 0.22 mmol) was added via syringe. After 45 minutes, the reaction mixture was quenched with an equal volume of saturated $NaHCO_3$ (note: gas evolution). The quenched mixture was extracted 3×5 ml $CH_2Cl_2$ and the organic layers were combined, dried over $Na_2SO_4$ and stripped to yield crude title product as an oil, 56.8 mg; $^1$H-NMR indicated some predominance of one diastereomer. By the same method the less polar isomer (21.9 mg, 0.043 mmol) was converted to a similar crude product mixture, 24.3 mg; $^1$H-NMR indicated some predominance of the other diastereomer. The two crude products were combined and chromatographed on silica gel to yield purified, title 1:1 product as an oil, 56.2 mg; tlc Rf 0.4 (1:6 ethyl acetate:hexane); $^1$H-NMR($CDCl_3$)delta(ppm), reflecting 1:1 diastereomeric product mixture: 6.40 and 6.30 (2d, J=3.1 and d, J=2.8, 1H), 6.11 and 5.89 (2s, 1H), 6.00–5.85 (m, 1H), 5.42–5.27 (m, 2H), 4.72 and 4.65 (d, J=5.9 and bd, J=6, 2H), 4.32–4.23 (m, 1H), 3.42–3.36 (m, 1H), 1.64 (s, 9H), 1.24 and 1.22 (d, J=6.2 and d, J=6.2, 3H), 0.88 and 0.86 (2s, 9H), 0.08 and 0.07 (2s, 3H), 0.06 and 0.05 (2s, 3H).

I claim:

1. A process for the preparation of a compound of the formula

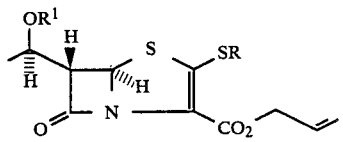

wherein R is ($C_1$–$C_5$) alkyl or

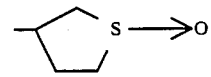

and $R^1$ is a conventional hydroxy-protecting group, which comprises (a) treating a compound of the formula

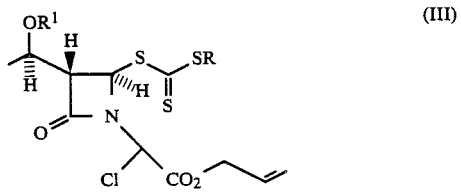

with base in a reaction-inert solvent at −80° to 40° C. to produce a mixture comprising a compound of the formula (I) and a compound of the formula

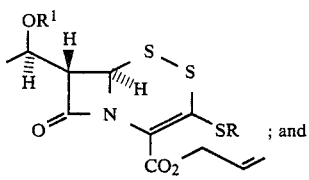

(b) desulfurization of the compound of the formula (II) with $(R^2O)_3P$ or $(R^3)_3P$ wherein each $R^2$ is the same or different and selected from $(C_1-C_4)$alkyl and each $R^3$ is the same or different and selected from $(C_1-C_4)$alkyl or phenyl, at $-50°$ to $40°$ C. in the same or a second reaction-inert solvent, to form additional compound of the formula (I).

2. A process of claim 1 wherein $R^1$ is t-butyldimethylsilyl.

3. A process of claim 2 wherein R is t-butyl.

4. A process of claim 2 wherein R is cis

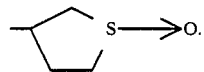

5. A process of claim 4 wherein the base in step (a) is 1,8-diazabicyclo[5.4.0]undec-7-ene.

6. A process of claim 5 wherein the solvent in step (a) is acetonitrile.

7. A process of claim 4 wherein the reagent in step (b) is triphenylphosphine.

8. A process of claim 4 wherein the solvent in step (b) is acetonitrile.

9. A process of claim 6 wherein the reagent in step (b) is triphenylphosphine.

10. The process of claim 9 wherein the solvent in step (b) is the same as in step (a).

11. A process of claim 1 which further comprises preparation of the compound of the formula (I) by the action of methanesulfonyl chloride and a tertiary amine on a compound of the formula

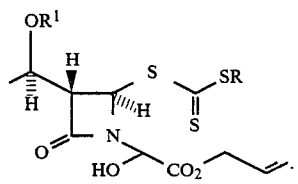

* * * * *